(12) United States Patent  
Suehira

(10) Patent No.: US 8,836,952 B2  
(45) Date of Patent: Sep. 16, 2014

(54) OPTICAL COHERENCE TOMOGRAPHIC IMAGING METHOD AND OPTICAL COHERENCE TOMOGRAPHIC IMAGING APPARATUS

(75) Inventor: Nobuhito Suehira, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/526,865

(22) Filed: Jun. 19, 2012

(65) Prior Publication Data

US 2012/0257165 A1 Oct. 11, 2012

(30) Foreign Application Priority Data

Jul. 30, 2008 (JP) ................................. 2008-196619

(51) Int. Cl.
*G01B 11/02* (2006.01)
*G01B 9/02* (2006.01)
*G01N 21/47* (2006.01)

(52) U.S. Cl.
CPC ........ *G01B 9/02091* (2013.01); *G01B 9/02044* (2013.01); *G01N 21/4795* (2013.01); *G01B 9/02083* (2013.01)
USPC ...................................................... 356/497

(58) Field of Classification Search
USPC ................ 356/479, 497; 250/227.19, 227.27; 351/205, 209, 210
See application file for complete search history.

(56) References Cited

U.S. PATENT DOCUMENTS

| 6,011,478 | A | 1/2000 | Suzuki et al. |
| 6,377,349 | B1 | 4/2002 | Fercher |
| 7,102,758 | B2 | 9/2006 | Wax |
| 7,237,898 | B1 * | 7/2007 | Hohla et al. .................. 351/246 |
| 7,301,644 | B2 * | 11/2007 | Knighton et al. ............. 356/479 |
| RE42,497 | E | 6/2011 | Wax |
| 8,233,152 | B2 * | 7/2012 | Suehira ........................ 356/497 |

FOREIGN PATENT DOCUMENTS

| JP | 11-23458 A | 1/1999 |
| JP | 11-325849 | 11/1999 |
| JP | 2001-141602 A | 5/2001 |
| JP | 2008-145375 A | 6/2008 |

OTHER PUBLICATIONS

Notification of Reasons for Refusal issued Oct. 23, 2012, in Japanese Application No. 2008-196619.

(Continued)

*Primary Examiner* — Michael A Lyons  
(74) *Attorney, Agent, or Firm* — Fitzpatrick, Cella, Harper & Scinto

(57) ABSTRACT

An optical tomographic diagnostic apparatus is characterized by executing a first step (S1) to acquire a wavelength spectrum, a second step (S2) to increase the number of elements of the wavelength spectrum, a third step (S3 and S4) to convert the wavelength spectrum into a wavenumber spectrum and to decrease the number of elements to provide a wavenumber spectrum of equal intervals, and a fourth step (S5) to acquire tomographic information of the object to be inspected from the wavenumber spectrum. As a result, a wavenumber spectrum of equal intervals can be obtained which is faithful to a physical phenomenon, and more accurate tomographic information can be obtained.

19 Claims, 6 Drawing Sheets

(56) References Cited

OTHER PUBLICATIONS

C. Dorrer, et al.: "Spectral resolution and sampling issues in Fourier-transform spectral interferometry". Optical Society of America, vol. 17, No. 10, pp. 1795-1802 (Oct. 2000).

N. A. Nassif, et al.: "In vivo high-resolution video-rate spectral-domain optical coherence tomography of the human retina and optic nerve". Optics Express, vol. 12, No. 3, pp. 367-376 (Feb. 9, 2004).

P. Li, et al.: "Spectral-domain optical coherence tomography and applications for biological imaging" International Symposium on, IEEE, PI (Oct. 1, 2006).

A.R. Tumlinson, et al.: "Inherent media dispersion compensation by FD-OCT". Proc. of SPIE, vol. 6429, pp. 1-11 (Feb. 7, 2007).

T.H. Chow, et al.: "Enhancement of Fourier domain optical coherence tomography images using discrete Fourier transform method". Proc. of SPIE, vol. 6847, pp. 1-8 (Feb. 18, 2008).

European Search Report in EP 09 16 5421, dated Nov. 24, 2009.

* cited by examiner

OPTICAL COHERENCE TOMOGRAPHIC IMAGING METHOD AND OPTICAL COHERENCE TOMOGRAPHIC IMAGING APPARATUS

This application is a divisional of U.S. patent application Ser. No. 12/500,254, filed Jul. 9, 2009, and allowed Mar. 29, 2012.

BACKGROUND OF THE INVENTION

1. Field of the Invention

The present invention relates to an optical coherence tomographic imaging apparatus, and in particular, to an optical coherence tomographic imaging apparatus having a coherent optical system used for medical application.

2. Description of the Related Art

Today, a variety of ophthalmic equipment using optical instruments is used. These are, for example, an anterior camera, a fundus camera, a confocal scanning laser ophthalmoscope (Scanning Laser Ophthalmoscope: SLO), etc. In particular, an optical coherence tomographic imaging apparatus (hereinafter referred to as an OCT apparatus) is to obtain a tomographic image of an object to be inspected at high resolution, and is now becoming a necessary and indispensable apparatus in specialty outpatient clinics for retina care.

The above-mentioned OCT apparatus uses low-coherence light as a light source. The light from the light source is divided into measurement light and reference light through a split optical path such as a beam splitter, etc. One of the light thus divided, the measurement light, is irradiated onto an object to be inspected such as an eye through a sample arm (measurement optical path), and return light thereof is guided to a detection position through a detection optical path. The return light is reflected light or scattered light that contains information on an interface in a direction of the light irradiated to the object to be inspected, etc. The other reference light is reflected by a reference mirror or the like through a reference arm (reference optical path), and is guided to the detection position. The return light and the reference light are caused to interfere with each other, and are analyzed so as to obtain information on a layer structure of the object to be inspected. In addition, it is possible to obtain a three-dimensional tomographic image by scanning low-coherence light in a two-dimensional manner.

Japanese patent application laid-open No. H11-325849 discloses an OCT apparatus used for medical application. Here, an optical spectrum is obtained by changing the position of a reference mirror three times in a discontinuous manner for the measurement of one point in an object to be inspected. It is possible to obtain a necessary optical spectrum in a desired area by performing one-dimensional scanning with the use of a scanner or the like. Finally, by analyzing these data, a two-dimensional tomographic image is obtained.

SUMMARY OF THE INVENTION

In Japanese patent application laid-open No. H11-325849, the position of the reference mirror is changed a plurality of times for the measurement of one point in the desired area. Such a scheme not only takes time for measurements but also requires precise position control of the reference mirror.

On the other hand, in an OCT apparatus used in the medical field, there is a method of measuring a sectional or tomographic layer by converting a wavelength spectrum from a spectroscope into a wavenumber spectrum with a reference mirror being fixed, and by further applying Fourier transform to the result thus converted. Such a scheme is called a Fourier domain OCT apparatus (FD-OCT), and includes a type using a wide-band light source, a type sweeping the wavelength of a light source, and so on. Generally, when the wavelength spectrum is converted into the wavenumber spectrum in the FD-OCT, the wavenumber spectrum does not have equal intervals because the wavenumber is the reciprocal of the wavelength. Thus, if a Fourier transform is directly carried out on the wavenumber spectrum as it is, accurate tomographic information might of course not be obtained. Therefore, a signal processing method has been demanded that is able to obtain more accurate tomographic information by converting a wavelength spectrum into a wavenumber spectrum of equal intervals faithful to a physical phenomenon.

Accordingly, the present invention has been made in view of the above-mentioned problems, and has for its object to obtain more accurate tomographic information.

A first aspect of the present invention is an optical coherence tomographic imaging method in an optical coherence tomographic imaging apparatus in which light from a light source is divided into measurement light and reference light through a split optical path, said measurement light is irradiated to an object to be inspected through a sample arm, and return light from said object to be inspected is guided to a detection position, and through a detection optical path, and said reference light is guided to said detection position through a reference arm, whereby a wavelength spectrum of interfering light caused by interference of said return light and said reference light both guided to said detection position, and a tomographic image of said object to be inspected is taken by a wavelength spectrum analysis unit that analyzes said wavelength spectrum, said optical coherence tomographic imaging method comprising:

a wavelength spectrum acquisition step to acquire the wavelength spectrum;

a wavenumber spectrum acquisition step to convert said wavelength spectrum into a wavenumber spectrum and to decrease the number of elements to provide a wavenumber spectrum of equal intervals; and a tomographic information acquisition step to acquire tomographic information of said object to be inspected from said wavenumber spectrum of equal intervals.

A second aspect of the present invention is an optical coherence tomographic imaging apparatus comprising:

a light source;

an optical system that divides light from the light source into measurement light and reference light, guides said measurement light to an object to be inspected, guides return light from said object to be inspected to a detection position, and guides said reference light to said detection position;

a wavelength spectrum acquisition unit that is arranged at said detection position, and acquires a wavelength spectrum from interference light caused by interference of said return light and said reference light; and a wavelength spectrum analysis unit that generates of a tomographic image of said object to be inspected from the wavelength spectrum thus acquired;

wherein said wavelength spectrum analysis unit executes:

a wavenumber spectrum acquisition step to convert said wavelength spectrum into a wavenumber spectrum and to decrease the number of elements to provide a wavenumber spectrum of equal intervals; and, a tomographic information acquisition step to acquire tomographic information of said object to be inspected from said wavenumber spectrum of equal intervals.

According to the present invention, in a Fourier domain optical coherence tomographic imaging apparatus, it is possible to obtain, from a wavelength spectrum, a wavenumber spectrum of equal intervals which is faithful to a physical phenomenon, and hence it is possible to obtain more accurate tomographic information.

BRIEF DESCRIPTION OF THE DRAWINGS

FIGS. 3A through 3D illustrate the appearance of signals in the first embodiment, wherein FIG. 3A is a view showing the intensity with respect to the wavelength, FIG. 3B is a view showing the intensity with respect to the wavelength after interpolation processing has been made, FIG. 3C is a view showing the intensity with respect to the wavenumber, and FIG. 3D is a view to which the intensity with respect to the wavenumber after resampling has been made.

FIGS. 6A through 6D illustrate the appearance of signals in the second embodiment, wherein FIG. 6A is a view illustrating an acquired wavenumber spectrum, FIG. 6B is a view illustrating what is obtained by Fourier transforming the wavenumber spectrum of FIG. 6A, FIG. 6C is a view illustrating expanding the number of elements by inserting zeros into the central portion of FIG. 6B, and FIG. 6D is a view illustrating a wavelength spectrum with an expanded number of elements obtained by inverse Fourier transforming the wavenumber spectrum of FIG. 6C.

DESCRIPTION OF THE EMBODIMENTS

In embodiments of the present invention, an optical coherence tomographic imaging apparatus has a unit that serves to divide or split light from a light source into measurement light and reference light through a split optical path. In addition, the measurement light can be irradiated to an object to be inspected through a sample arm (measurement optical path), and return light of the measurement light from the object to be inspected can be guided to a detection position through a detection optical path. Further, the reference light is guided to the detection position through the reference arm (reference optical path), so that the return light guided to the detection position and the reference light can be interfered or cohered with each other to provide a wavelength spectrum of coherent light. A tomographic image can be taken by means of a wavelength spectrum analysis unit. Furthermore, the wavelength spectrum analysis unit executes a first step to acquire the wavelength spectrum. Then, the unit also executes a second step to increase the number of elements of the wavelength spectrum. Further, the unit executes a third step to convert the wavelength spectrum into a wavenumber spectrum, and to decrease the number of elements to provide a wavenumber spectrum of equal intervals. In addition, the unit can execute a fourth step to acquire tomographic information of the object to be inspected from the wavenumber spectrum of equal intervals. Here, note that in case where the number of elements of the wavenumber spectrum in the first step is sufficiently large, the second step can be omitted.

Now, reference will be made to specific embodiments of the present invention.

First Embodiment

In a first embodiment of the present invention, reference will be made to an optical coherence tomographic imaging apparatus (hereinafter also referred to as an OCT apparatus) to which the present invention is applied, while using the accompanying drawings.

<Construction of Optical System>

Figure 1:
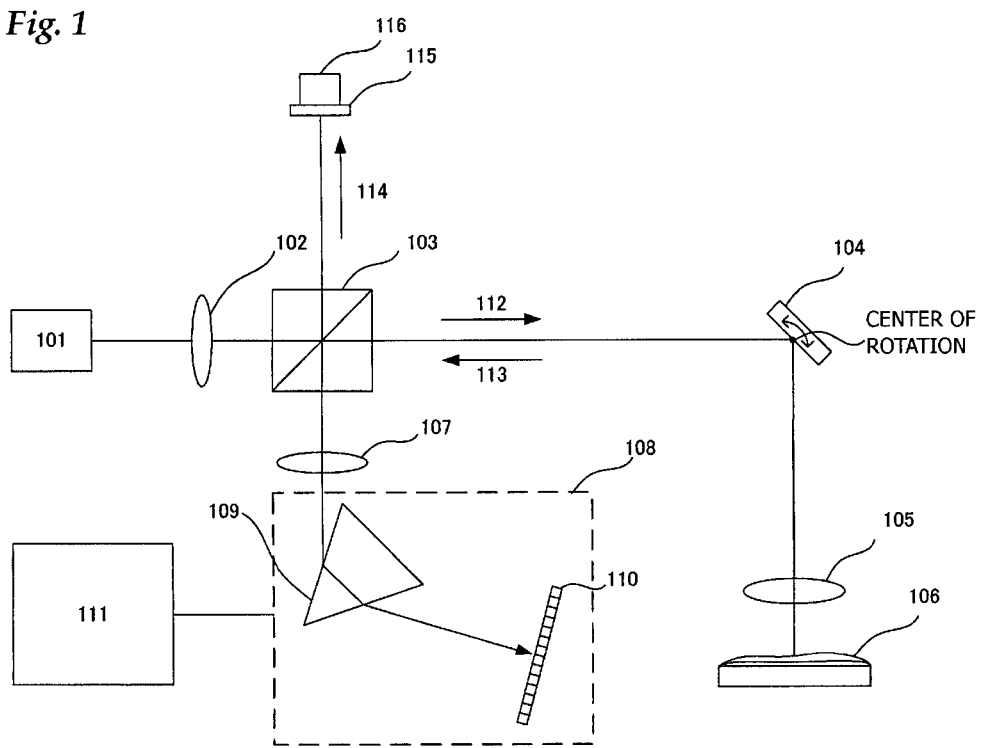
FIG. 1 is a view for explaining an optical system of an optical tomographic diagnostic apparatus in a first embodiment of the present invention.

First of all, the construction of the OCT apparatus will be roughly described while referring to FIG. 1. The light emitted from a light source 101 is divided into measurement light 112 and reference light 114 by means of a beam splitter 103 through a lens 102. The measurement light 112 reaches an object 106 to be inspected through an XY scanner 104 and an object lens 105. A transparent film is formed on the object 106 to be inspected. Return light 113 scattered and reflected on a surface and an interface thereof returns while passing through the object lens 105, the XY scanner 104, and the beam splitter 103 in this order. In addition, the return light further reaches a spectroscope 108 arranged at a detection position through an imaging lens 107. On the other hand, the reference light 114 is reflected by a reference mirror 115. Here, note that the reference mirror 115 can adjust an optical path length by a position adjusting mechanism 116. The reference light 114 is combined with the return light 113 by means of the beam splitter 103.

The light source 101 is a SLD (Super Luminescent Diode) that is a typical low-coherence light source. For instance, the SLD has a wavelength of 830 nm and a bandwidth of 50 nm. Here, note that the bandwidth influences resolution in the direction of the optical axis of an tomographic image to be obtained and hence becomes an important parameter. In addition, although the SLD is selected here for the light source, any kind of light source can be used which need only be able to emit low-coherence light, and an ASE (Amplified Spontaneous Emission) or the like can be used. Of course, other light sources such as a halogen lamp, etc., can be used depending upon the contents of the object to be inspected. However, the wavelength also influences resolution in the horizontal direction of the tomographic image to be obtained, so it is desirable to use a short wavelength in case where horizontal resolution is important.

The spectroscope 108 is composed of a prism 109, an image pickup element 110, and so on, and it serves to disperse the measurement light into spectrum. For the image pickup element 110, there can be adopt a CCD type line sensor. The light thus dispersed is acquired as wavelength spectral data by the image pickup element 110 in the spectroscope 108.

The spectral data imaged by the image pickup element 110 is analyzed by a computer 111. That is, the computer 111 corresponds to a wavelength spectrum analysis unit. Of course, the computer has not only an analytic function but also functions to store data, to display images, to issue a measurement command, and so on. In addition, a section pattern or image of the object to be inspected can be obtained by raster scanning the measurement light on the object to be inspected in a direction perpendicular to its optical axis under the control of the computer 111. The computer 111 is composed of a CPU, a memory and so on, and achieves the above-mentioned functions by executing a program by means of the CPU. However, part or all of the above-mentioned respective functions can be achieved by dedicated hardware.

<Signal Processing>

Figure 2:
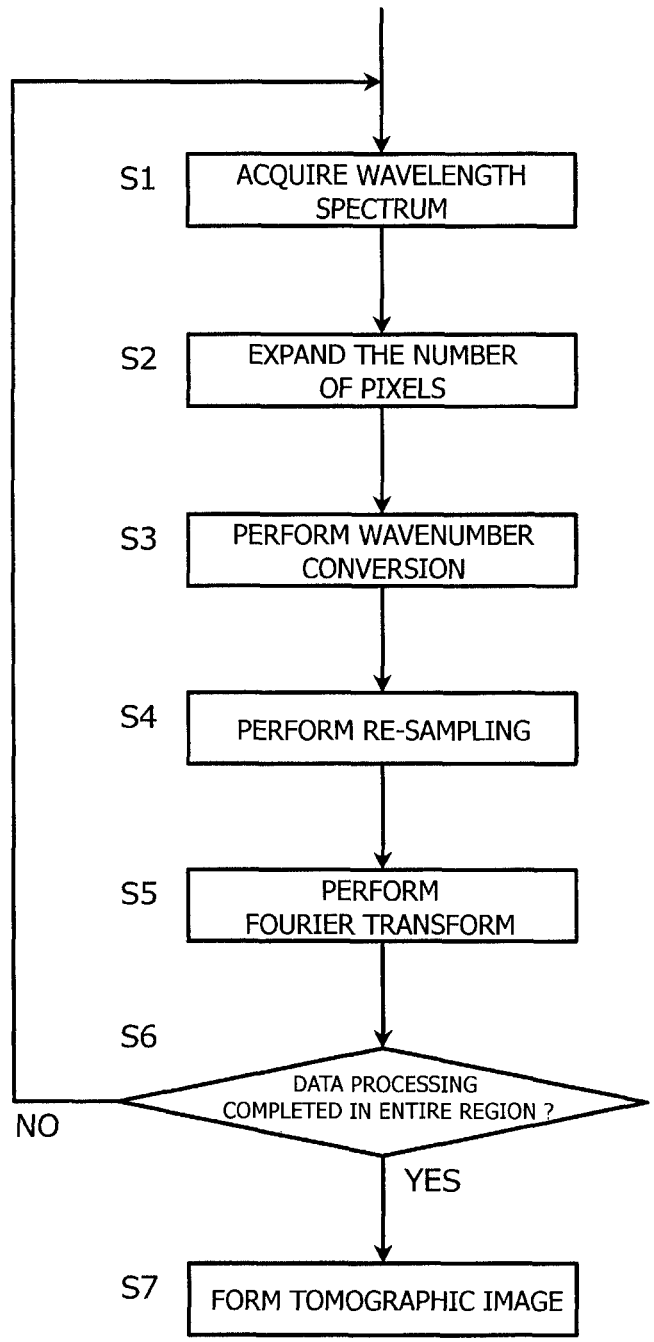
FIG. 2 is a flow chart illustrating a flow of signal processing in the first embodiment of the present invention.

A signal processing step of the present invention will be explained by using FIG. 2.

Figure 3A:
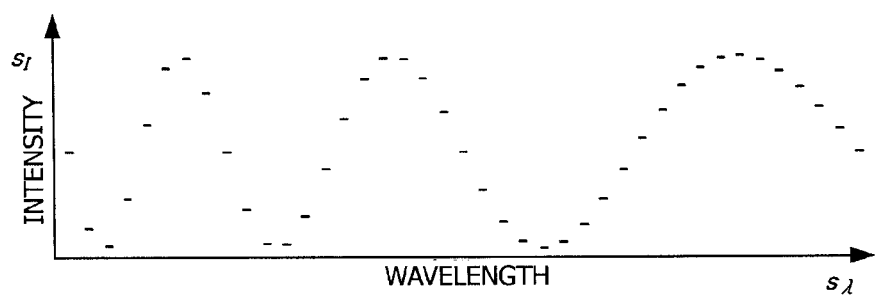

First of all, in a step of S1, a wavelength spectrum is acquired from the spectroscope 108 (wavelength spectrum acquisition step). The number of samplings at this time is N (e.g., 2,048), which is the number of pixels of the image pickup element 110. Information of the spectrum includes wavelengths and intensities for the wavelengths. First, the wavelengths are decided by the characteristics of the spectroscope 108, so they are beforehand stored in a one-dimensional array. The intensity data thus acquired is stored in another one-dimensional array. Here, an i-th wavelength component and an i-th intensity component are denoted by $s_\lambda(i)$, $s_I(i)$, respectively, and this combination is presented as $(s_\lambda(i), s_I(i))$ for the sake of convenience. An element i has a range of from 0-th to (N−1)th. FIG. 3A diagrammatically illustrates a graph of intensity with respect to wavelength. The sampling intervals are equal with respect to wavelength, and a minimum value of wavelength is 805 nm, and a maximum value thereof is 855 nm. Here, note that the sampling intervals might not be equal with respect to wavelength depending upon the characteristics of the spectroscope 108. In such a case, appropriately interpolated elements can be used.

Then, in a step of S2, the wavelength spectrum is interpolated in such a manner that the number of sampling points (the number of elements) is increased by M times (e.g., 16 times) to generate wavelength spectral data (an element number increasing step). As such an interpolation method, there is enumerated a linear interpolation or the like. An i-th element before interpolation becomes an M·i-th element after being interpolated. Here, note that M·i denotes a multiplication of M and i. Elements between the M·i-th element and M·(i+1)-th element are able to be denoted as (M·i+j)-th elements. Here, i is in the range of from 0 to N−1, and j is in the range of from 0 to M−1, and so it is possible to denote all the M·N elements by such an expression. In the case of the linear interpolation, an (M·i+j)-th element is represented as shown in the following mathematical expression 1 by using $(s_\lambda(i), s_I(i))$ and $(s_\lambda(i+1), s_I(i+1))$.

$$(s'_\lambda(M \cdot i + j), s'_I(M \cdot i + j)) = \quad \text{(Expression 1)}$$

$$\frac{M-j}{M}(s_\lambda(i), s_I(i)) + \frac{j}{M}(s_\lambda(i+1), s_I(i+1))$$

Figure 3B:
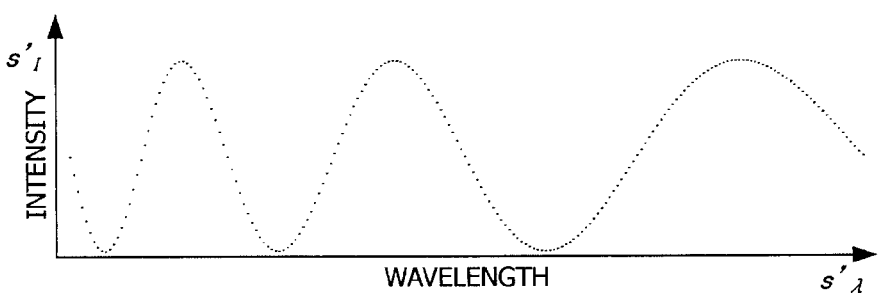

FIG. 3B diagrammatically illustrates a graph of the intensity to the wavelength after interpolation. The sampling intervals are equal, and the number of elements is M times as many as the original number thereof (before interpolation), thus resulting in high density sampling.

In a step of S3, the wavelength spectrum is converted into a wavenumber spectrum (a wavenumber spectrum acquisition step). The wavenumber is a reciprocal of the wavelength. Accordingly, the wavenumber spectrum is represented as shown in the following mathematical expression 2 by denoting an element of an i-th wavenumber and an i-th intensity as $(p_w(i), p_I(i))$. That is, the order of intensity is inverted when sorted in an ascending order with respect to the wavenumber. Here, note that the number of elements is M·N ranging from 0 to (M·N−1).

$$(p_w(i), p_I(i)) = \left(\frac{1}{s'_\lambda(M \cdot N - 1 - i)}, s'_I(M \cdot N - 1 - i)\right) \quad \text{(Expression 2)}$$

Figure 3C:
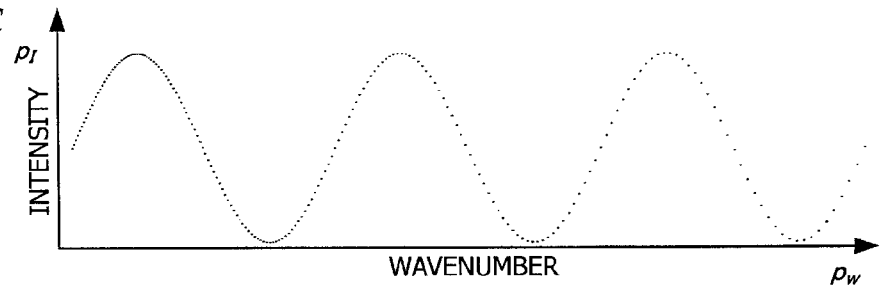

FIG. 3C diagrammatically illustrates a graph of the intensity to the wavenumber. The sampling interval is equal with respect to the wavelength, so when the wavelength is converted into the wavenumber, the sampling density becomes higher in accordance with the decreasing wavenumber.

In a step of S4, resampling is performed. The number of samplings between $p_w(0)$ and $p_w(M \cdot N-1)$ is set to P·N, and elements at that time are denoted by $(u_w(k), u_I(k))$. Here, P is 2, for instance. At this time, $u_w(k)$ is represented by the following mathematical expression 3.

$$u_w(k) = \frac{p_w(M \cdot N - 1) - p_w(0)}{P \cdot N - 1} k + p_w(0) \quad \text{(Expression 3)}$$

On the other hand, $u_I(k)$ is decided as follows. According to this algorithm, first of all, $p_w(j)$, being nearest to $u_w(k)$, is found, and $p_I(j)$ corresponding to $p_w(j)$ thus found is substituted for $u_I(k)$.

That is, $p_w(j)$ satisfying the following expression 4 is found.

$$p_w(j) \leq u_w(k) < p_w(j+1) \quad \text{(Expression 4)}$$

Then, $u_I(k)$ is decided as shown in the following mathematical expression 5.

$$\begin{cases} u_w(k) - p_w(j) < p_w(j+1) - u_w(k), & u_I(k) = p_I(j) \\ u_w(k) - p_w(j) \geq p_w(j+1) - u_w(k), & u_I(k) = p_I(j+1) \end{cases} \quad \text{(Expression 5)}$$

Here, note that if M is sufficiently larger with respect to P, sampling with a sufficiently high degree of accuracy can be performed according to this method. If it is not so, $u_I(k)$ can be calculated by performing a linear interpolation by the use of $p_I(j)$ and $p_I(j+1)$ in accordance with the value of $u_w(k)$.

Figure 3D:
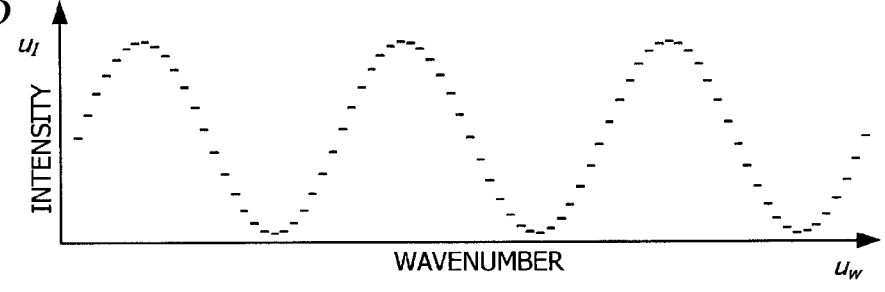

FIG. 3D diagrammatically illustrates a graph of the intensity with respect to the wavenumber sampled at equal intervals. In conventional methods, the wavelength spectrum has been converted into the wavenumber spectrum without changing the number of elements. The wavelength is the reciprocal of the wavenumber, and has an unequal interval, so it has been difficult to obtain the wavenumber spectrum of equal intervals that is faithful to a physical phenomenon necessary for analysis. On the other hand, in a method of the present invention, the wavenumber spectrum of equal intervals can be obtained, so it becomes able to perform an accurate analysis. In addition, when the number of data is increased from N to N·M, and when the wavelength is converted into the wavenumber, the number of data is decreased to N·P. Here, by making the value of M sufficiently large, it is possible to acquire the wavenumber spectrum more accurately.

In a step of S5, a Fourier transform is carried out so that a tomographic layer of the object to be inspected is measured (tomographic information acquisition step). Tomographic data thus measured is stored in succession into the memory or hard disk of the computer.

In a step of S6, it is determined whether data processing has been completed in the entire inspection region. When not completed, a return is made to S1, and data processing is performed until it has been completed in the entire inspection region.

In a step of S7, a three-dimensional tomographic image can be formed from the tomographic data calculated in the step of S5.

In the method of the present invention, the number of elements is N in the step of S1, M·N in the step of S2, and N·P in the step of S4, but there is no need to set the number of elements to multiples of N. In other words, the number of elements in the step of S2 need only be larger than or equal to that in the step of S1, and the number of elements in the step of S3 need only be less than that in the step of S2. In addition, if there are a sufficient number of elements in the step of S1, the step of S2 can be skipped, and in the step of S4, the number of elements can be made less than the number of elements in the step of S1. Of course, after the number of elements in the step of S2 has been increased to a value more than the number of elements of steps of S1, the number of elements in the step of S4 can be decreased to a value less than the number of elements in the step of S1. The time required in and after a step of S5 can be shortened by decreasing the number of elements in the step of S4. In addition, a fast Fourier transform (FFT) can be performed by setting the numbers of elements in the steps of S1, S2 and S4 to the values of powers of 2. Here, note that the Fourier transform of discrete values is called DFT, and the FFT is a special case thereof.

Although the above-mentioned signal processing can be executed by a program built into a general-purpose computer, a special LSI can of course be used as separate hardware. In addition, an FPGA (Field Programmable Gate Alley) or the like can also be used.

Second Embodiment

In a second embodiment of the present invention, reference will be made to an optical system in an ophthalmic optical coherence apparatus to which the present invention is applied, by using FIG. 4.

<Construction of Optical System>

Figure 4:
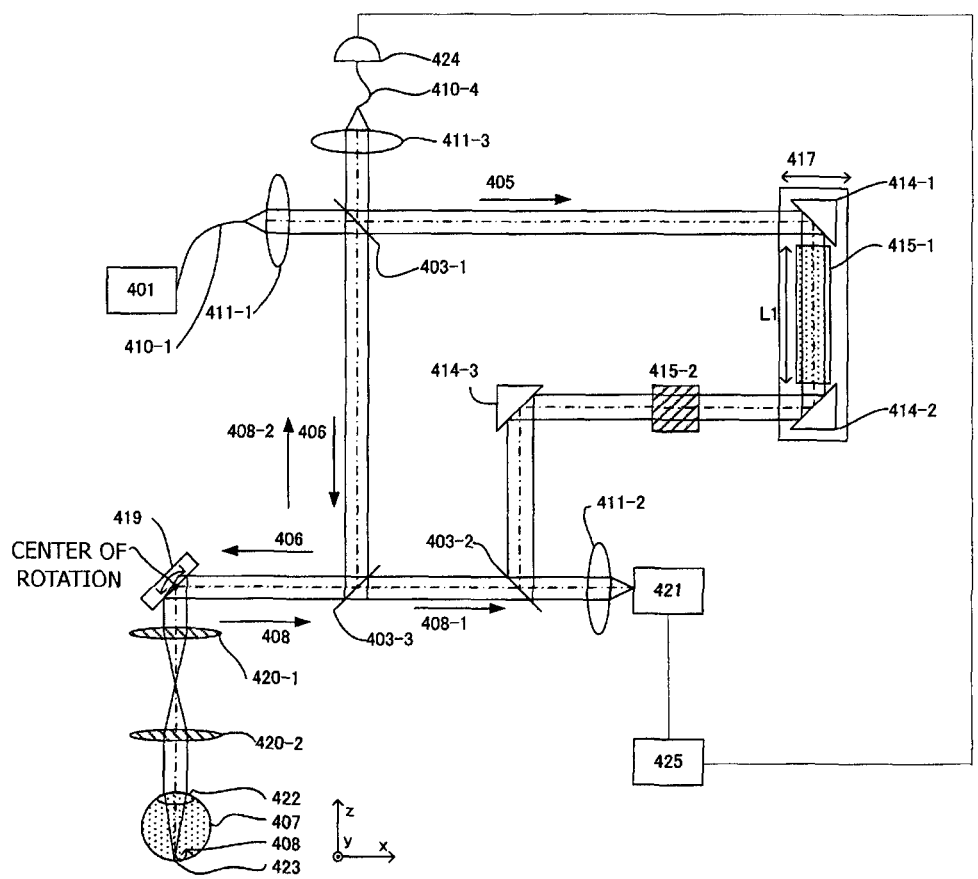
FIG. 4 is a view for explaining an optical system of an ophthalmic optical tomographic diagnostic apparatus in a second embodiment of the present invention.

FIG. 4 illustrates constructing a Mach-Zehnder interference system as a whole. The light emitted from a light source 401 is guided to a lens 411-1 through a single-mode fiber 410-1. Further, the light is divided into reference light 405 and measurement light 406 by means of a beam splitter 403-1. The measurement light 406 is returned as return light 408 through reflection or scattering by means of an eye 407 which is an object to be inspected, after which the return light is combined with the reference light 405 by means of a beam splitter 403-2 to enter a spectroscope 421. Here, the light source 401 is an SLD (Super Luminescent Diode) which is a typical low-coherence light source. In view of the fact that the eye is measured, near-infrared light is suitable for the wavelength to be used.

Reference will be made to an optical path of the reference light 405. The reference light 405 divided by the beam splitter 403-1 is caused to successively enter mirrors 414-1 through 414-3, whereby the light is changed in its direction to enter the spectroscope 421 through the beam splitter 403-2. Here, 415-1 and 415-2 denote dispersion compensation glasses, respectively. The length of the dispersion compensation glass 415-1 is denoted by L1, and is preferably equal to twice the depth of a general eye. The dispersion compensation glass 415-1 compensates for dispersion of the measurement light 406 with respect to the reference light 405 when the measurement light 406 goes to and from an eye 407. Here, L1 is set equal to 46 mm (L1=46 mm), twice the diameter of an average Japanese eyeball of 23 mm. Further, 417 denotes an electric stage which can be moved in a direction shown by an arrow, and the optical path length of the reference light 405 can be adjusted and controlled. The dispersion compensation glass 415-2 is intended for dispersion compensation of the lenses 420-1, 420-2 used to scan the eye 407.

Reference will be made to the optical path of the measurement light 406. The measurement light 406 divided by the beam splitter 403-1 is reflected by a beam splitter 403-3, and is then incident on a mirror of an XY scanner 419. The XY scanner 419 raster scans a retina 423 in a direction perpendicular to the optical axis of the measurement light. In addition, the center of the measurement light 406 is adjusted so as to coincide with the axis of rotation of the mirror of the XY scanner 419. Lenses 420-1, 420-2 constitute an optical system for scanning the retina 423, and have a role to scan the measurement light 406 on the retina 423 with the cornea 422 acting as a fulcrum. Here, the focal distances of the lenses 420-1, 420-2 are 50 mm and 50 mm, respectively. When the measurement light 406 is incident on the eye 407, the return light 408 is generated due to the reflection and scattering of the measurement light from the retina 423. Further, the return light 408 is divided into return light 408-1 and return light 408-2 by means of the beam splitter 403-3, so that the one return light 408-1 is guided to the spectroscope 421. Here, the spectroscope 421 is a diffraction grating type spectroscope, and an image pickup element therein is a CCD type line sensor. Data such as a wavelength spectrum, etc., acquired by the spectroscope 421 is taken into a computer 425.

In addition, the other return light 408-2 is guided to a detector 424 while passing through the beam splitter 403-1. The detector 424 outputs a signal which is electrically taken into the computer 425, similar to an interference signal, so that the intensity of the return light 408-2 can be recorded and displayed. Also, the signal obtained by the detector 424 is an intensity signal of the return light 408-2 due to the reflection or scattering on the retina 423, and does not have depth resolution. The detector 424 is, for example, an APD (Avalanche Photo Diode) that is a sensor of high speed and high sensitivity.

<Signal Processing>

Figure 5:
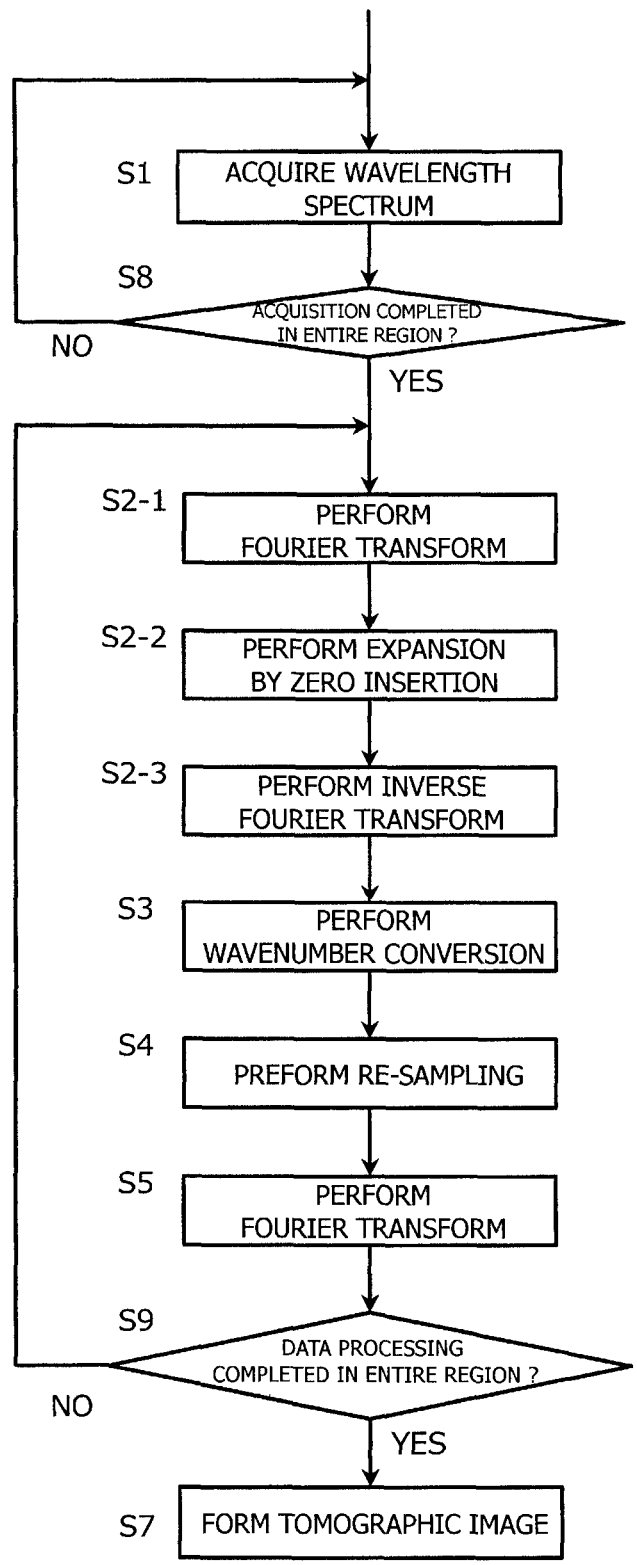
FIG. 5 is a flow chart illustrating a flow of signal processing in the second embodiment of the present invention.

Reference will be made to differences in signal processing between this second embodiment and the above-mentioned first embodiment, while referring to FIGS. 5 and 6. The signal processing method of this second embodiment is mainly different from the method of the first embodiment in the features of data being first acquired and of how to expand the range. Here, note that FIG. 5 is a flow chart illustrating the flow of the signal processing in this embodiment, and FIGS. 6A-6D are views illustrating the appearance of signals in the signal processing.

A wavelength spectrum (FIG. 6A) is acquired in a step of S1, similar to the first embodiment. Here, note that the wavelength and intensity of an i-th element are denoted by $s_\lambda(i)$ and $s_I(i)$, respectively. The data of the spectrum thus acquired is sequentially stored in a memory or hard disk of the computer 425.

In a step of S8, it is determined whether the acquisition of a wavelength spectrum at each position in an inspection region has been completed. When completed in the entire inspection region, the flow of processing proceeds to a step of S2-1. In case where the signal processing takes much time, it is important to perform the acquisition of data in the inspection region in priority to the signal processing, For example, it is a case where the object to be inspected is a moving object such as an eye.

Figure 6A:
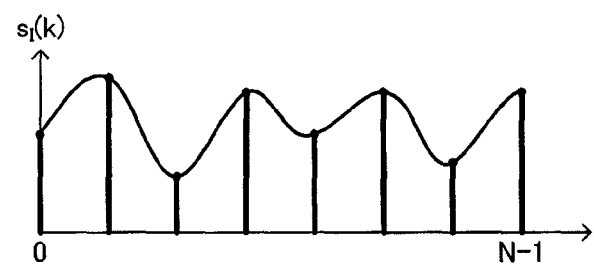
Figure 6B:
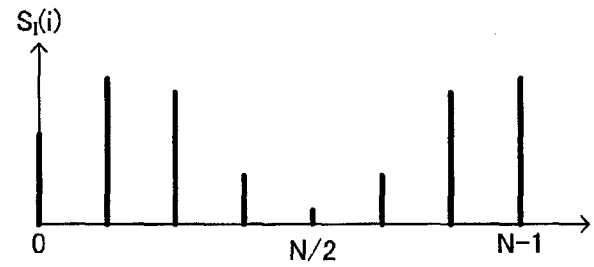

In the step of S2-1, the wavelength spectral data is subjected to Fourier transformation. An intensity element $S_I(i)$ becomes as shown by the following mathematical expression 6. The signal after the Fourier transformation becomes as shown in FIG. 6B. In general, the intensity of an i-th element and the intensity of an (N−i)-th element are the same, and these elements become mirror images with respect to a boundary of N/2. In addition, a 0-th element is a constant component.

$$S_I(i) = \sum_{k=0}^{N-1} s_I(k) e^{-j\frac{2\pi k i}{N}} \quad \text{(Expression 6)}$$

Here, note that in case where spectral data has not equal intervals with respect to the wavelength due to the characteristic of the spectroscope 421, $s_\lambda(i)$ and $s_I(i)$ interpolated at equal intervals can be used. A criterion for such a determination is, for instance, when there is an error of 1% or more for spectral data of unequal intervals as compared with the case in which it is divided at equal intervals.

Figure 6C:
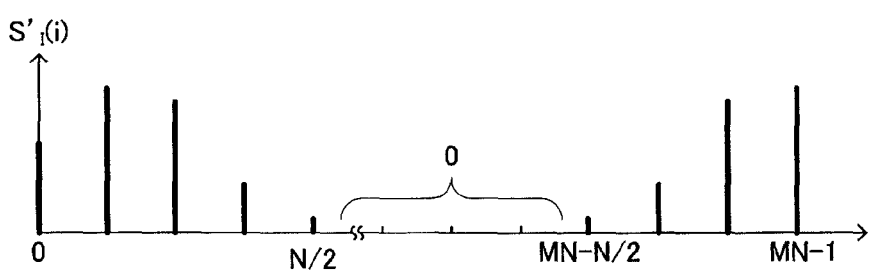

In a step of S2-2, the spectral data is divided into two by a boundary of an (N/2)-th element of $S_I(i)$, and zeros are inserted therein in such a manner that the number of elements is expanded to MN, as shown by the following mathematical expression 7 (M is an integer of two or more). Of course, i is an integer. The spectral data of which the number of elements is expanded is illustrated in FIG. 6C. Here, note that when N/2 is an integer, the (N/2)-th element is used twice. Accordingly, the Fourier transform of an i-th element coincides with the Fourier transform of an (MN−i)-th element. However, data in the vicinity of (N/2)-th element is a limitation that can be restored according to a sampling theorem, so the system is desirable in which such data becomes 0.

$$S'_I(i) = \begin{cases} S_I(i), & 0 \le i \le N/2 \\ 0, & N/2 < i < M \cdot N - N/2 \\ S_I(i - M \cdot N + N) & M \cdot N - N/2 \le i \le M \cdot N - 1 \end{cases} \quad \text{(Expression 7)}$$

Figure 6D:
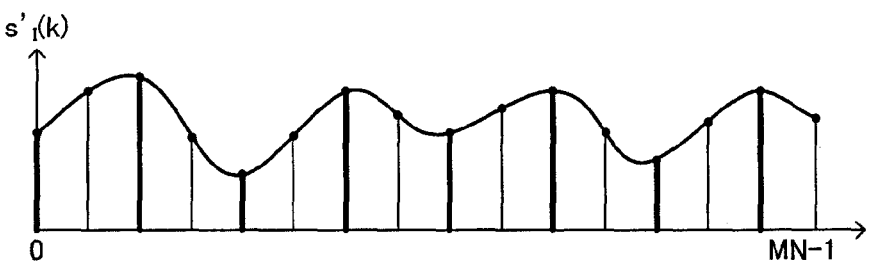

In a step of S2-3, the wavelength spectrum in the step of S2-1 is interpolated by inverse Fourier transforming this $S'_I(i)$, as shown in FIG. 6D. The spectrums $(s'_\lambda(i), s'_I(i))$ at that time are represented by the following mathematical expressions 8 and 9, respectively. That is, the number of elements for $s'_\lambda(i)$ is increased to M times its original value by dividing wavenumber ranges at equal intervals, similar to the first embodiment. $s'_I(i)$ can be obtained by inverse Fourier transforming $S'_I(i)$, and further increasing the number of elements to M times its original value.

$$s'_\lambda(k = M \cdot i + j) = \frac{M - j}{M} s_\lambda(i) + \frac{j}{M} s_\lambda(i + 1) \quad \text{(Expression 8)}$$

$$s'_I(k) = \quad \text{(Expression 9)}$$
$$M \times \frac{1}{M \cdot N} \sum_{n=0}^{M \cdot N - 1} S'_I(n) e^{j\frac{2\pi nk}{M \cdot N}} = \frac{1}{N} \sum_{n=0}^{M \cdot N - 1} S'_I(n) e^{j\frac{2\pi nk}{M \cdot N}}$$

Here, note that $s'_I(k)$ has a relation as shown by the following mathematical expression 10.

$$s'_I(M \cdot k) = \frac{1}{N} \sum_{i=0}^{N-1} S_i(i) e^{j\frac{2\pi ik}{N}} = s_I(k) \quad \text{(Expression 10)}$$

That is, an M·k-th element of $s'_I(i)$ is obtained by applying an inverse Fourier transform to $S_I(i)$, and coincides with a k-th element of $s_I(i)$. Of course, interpolation is performed in a range therebetween.

Here, note that in case where Fourier transform is used, an (M·N−1)-th element might sometimes be far apart from an (M·N−2)-th element. In that case, a window function such as a Hamming window, a triangular window, a Blackman window or the like can be used. By using such a window function beforehand, it becomes unnecessary to employ any window function when Fourier transformation is performed in a step of S5. In addition, in case where such processing is inconvenient, the (M·N−1)-th element can be replaced with one which is calculated by appropriately using the (M·N−2)-th element and the original (N−1)-th element.

In a step of S3, the wavelength spectrum is converted into a wavenumber spectrum in the same way as the first embodiment.

In a step of S4, resampling is carried out so that the number of elements becomes N·P at equal intervals with respect to the wavenumber.

In a step of S5, tomographic information can be obtained by Fourier transforming intensity data of N·P pixels.

In a step of S9, it is determined whether data processing has been completed in the entire inspection region. The results of the data processing are stored in the memory or the hard disk in a successive manner.

In a step of S7, a tomographic image is formed from the result calculated in the step of S5. After a spectrum has been taken at each position in the inspection region in the step of S1, signal processing in and after the step of S2-1 is carried out. Accordingly, the measurement time of the eye can be made a minimum.

Here, reference will be made to an example in which the signal processing method according to the second embodiment is suitable for an OCT apparatus. In case where light is incident from a medium of a low refractive index to a medium of a high refractive index, a condition under which the light reflected on the reference mirror interferes with the light reflected on the retina is represented as a constructive condition by the following mathematic expression 11 using a refractive index n, a difference d in the spatial distance between the reference mirror and the retina, an integer m, and a wavenumber k.

$$k_m = \frac{m}{2nd} \quad \text{(Expression 11)}$$

Also, the above-mentioned condition is represented as a destructive condition by the following mathematic expression 12. Here, note that in case where light is reflected when incident from a medium of a high refractive index to a medium of a low refractive index, the constructive condition and the destructive condition are reversed.

$$k_{m+0.5} = \left(m + \frac{1}{2}\right)\frac{1}{2nd} \quad \text{(Expression 12)}$$

In this manner, the intensity is represented as a periodic function with respect to the wavenumber. It is due to this reason that in the step of S5, the tomographic image can be obtained by performing Fourier transformation. Of course, the intensity is periodic with respect to the wavelength, and hence it can be said that the method according to this second embodiment is more suitable than a linear interpolation method.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-196619, filed on Jul. 30, 2008, which is hereby incorporated by reference herein in its entirety.

What is claimed is:
1. A method comprising:
increasing the number of elements of a wavelength spectrum of interfering light by using an analysis unit, wherein said interfering light is caused by interference of return light from an eye irradiated by measurement light via a scanning unit and reference light corresponding to said measurement light, wherein the scanning unit scans the measurement light on a retina of the eye with a cornea acting as a fulcrum;
converting the wavelength spectrum into a wavenumber spectrum by using an analysis unit after the number of elements of the wavelength spectrum is increased; and
acquiring a tomographic image of the retina based on said wavenumber spectrum by using an analysis unit.

2. The method according to claim 1, further comprising a step of decreasing the number of elements, wherein sampling points are decided in such a manner that the intervals of wavenumbers are equal to each other, and an intensity at each sampling point is obtained as an intensity at the nearest wavenumber to a wavenumber at said each sampling point in the wavenumber spectrum converted from the wavelength spectrum.

3. The method according to claim 1, further comprising a step of decreasing the number of elements, wherein sampling points are decided in such a manner that the intervals of the wavenumbers become equal to each other, and an intensity at each sampling point is obtained as intensities at two nearest wavenumbers to a wavenumber at said each sampling point in the wavenumber spectrum converted from the wavelength spectrum.

4. The method according to claim 1, wherein
in said step of increasing the number of elements, a Fourier transform is applied to said wavelength spectrum to obtain element SI(i), S'I(i) is obtained in which the number of elements in SI(i) after the Fourier transformation is expanded, as shown by the following expression, and a wavelength spectrum of which the number of elements is increased by inverse Fourier transforming S'I(i)

$$S'_I(i) = \begin{cases} S_I(i), & 0 \le i \le N/2 \\ 0, & N/2 < i < M \cdot N - N/2 \\ S_I(i - M \cdot N + N) & M \cdot N - N/2 \le i \le M \cdot N - 1 \end{cases}$$

where N is the number of elements of SI(i), and M is an integer of two or more.

5. The method according to claim 1, further comprising a step of decreasing the number of elements of the wavenumber spectrum by using an analyzing unit, wherein the decreased number of elements is a power of 2.

6. The method according to claim 1, further comprising the steps of:
acquiring the wavelength spectrum before the number of elements is increased; and
decreasing the number of elements, the number of elements of the spectrum is decreased to less than the number of elements of the spectrum before said increase.

7. The method according to claim 1, further comprising a step of acquiring the wavelength spectrum before the number of elements of the wavelength spectrum is increased, wherein
in said step of acquiring the wavelength spectrum, after the wavelength spectrums are acquired at respective positions in an inspection region of the retina, the number of elements on each of the wavelength spectrums is increased.

8. The method according to claim 1, wherein the step of increasing the number of elements comprises interpolating the wavelength spectrum.

9. The method according to claim 1, further comprising a step of:
decreasing the number of elements of the wavenumber spectrum so as to acquire a wavenumber spectrum of substantially equal intervals by using an analysis unit.

10. A non-transitory computer readable medium containing program instructions for a computer to execute the method according to claim 1.

11. The method according to claim 1, further comprising a step of:
decreasing the number of elements of the wavenumber spectrum by using an analysis unit.

12. An apparatus comprising:
an increasing unit configured to increase the number of elements of a wavelength spectrum of interfering light, wherein said interfering light is caused by interference of return light from an eye irradiated by measurement light via a scanning unit and reference light corresponding to said measurement light, wherein the scanning unit scans the measurement light on a retina of the eye with a cornea acting as a fulcrum;
a converting unit configured to convert the wavelength spectrum into a wavenumber spectrum after the number of elements of the wavelength spectrum is increased; and
an acquisition unit configured to acquire a tomographic image of the retina based on said wavenumber spectrum.

13. An apparatus according to claim 12, wherein said increasing unit is configured to interpolate the number of elements of the wavelength spectrum.

14. An apparatus according to claim 12, further comprising a decreasing unit configured to decrease the number of elements of the wavenumber spectrum so as to acquire the wavenumber spectrum of substantially equal intervals.

15. An apparatus according to claim 14, wherein the decreased number of elements decreased by said decreasing unit is a power of 2.

16. An apparatus according to claim 12, further comprising a display control unit configured to display said tomographic image on a display unit.

17. An apparatus according to claim 12, further comprising a determination unit configured to determine whether tomographic image is acquired at respective positions in an inspection region of the retina.

18. An apparatus according to claim 12, further comprising:
a wavelength spectrum acquisition unit configured to acquire said wavelength spectrum, and
a determination unit configured to determine whether said wavelength spectrum is acquired at respective positions in an inspection region of the retina.

19. An apparatus according to claim 12, further comprising:
a decreasing unit configured to decrease the number of elements of the wavenumber spectrum.

* * * * *